(12) United States Patent
Arendash et al.

(10) Patent No.: US 11,794,028 B2
(45) Date of Patent: Oct. 24, 2023

(54) TRANSCRANIAL ELECTROMAGNETIC TREATMENT

(71) Applicant: NeuroEM Therapeutics, Inc., Phoenix, AZ (US)

(72) Inventors: Gary W. Arendash, Phoenix, AZ (US); Robert Baranowski, Escondido, CA (US)

(73) Assignee: NeuroEM Therapeutics, Inc., Tampa Bay, FL (US)

( * ) Notice: Subject to any disclaimer, the term of this patent is extended or adjusted under 35 U.S.C. 154(b) by 97 days.

(21) Appl. No.: 16/936,152

(22) Filed: Jul. 22, 2020

(65) Prior Publication Data

US 2020/0346028 A1  Nov. 5, 2020

Related U.S. Application Data

(63) Continuation-in-part of application No. 14/205,333, filed on Mar. 11, 2014, now Pat. No. 10,765,879.
(Continued)

(51) Int. Cl.
*A61N 1/04* (2006.01)
*A61N 2/00* (2006.01)
(Continued)

(52) U.S. Cl.
CPC .......... *A61N 2/006* (2013.01); *A61N 1/0456* (2013.01); *A61N 1/0476* (2013.01);
(Continued)

(58) Field of Classification Search
CPC .... A61N 2/006; A61N 1/0456; A61N 1/0476; A61N 1/36082; A61N 1/378; A61N 1/40;
(Continued)

(56) References Cited

U.S. PATENT DOCUMENTS 5,686,516 A    11/1997  Tzur
6,248,126 B1 *  6/2001  Lesser ...................... A61F 7/12
                                                        607/113
(Continued)

FOREIGN PATENT DOCUMENTS

AU    2015388475 A1    8/2017
AU    2017363200 A1    6/2019
(Continued)

OTHER PUBLICATIONS

Arendash G.W.; "Review of the Evidence that Transcranial Electromagnetic Treatment will be a Safe and Effective Therapeutic Against Alzheimer's Disease"; Journal of Alzheimer's Disease; 2016; 753-771; DOI 10.3233/JAD-160165.
(Continued)

*Primary Examiner* — Amanda K Hulbert
*Assistant Examiner* — Natasha Patel
(74) *Attorney, Agent, or Firm* — Nathan G. Guymon, Esq.; Bamert Regan PLLC

(57) ABSTRACT

In one example in accordance with the present disclosure a method is described. According to the method, an emitter of a transcranial electromagnetic treatment (TEMT) system is positioned at a location relative to a head of a patient such that the emitter emits an electromagnetic frequency signal toward the head of the patient. The emitter is activated to apply TEMT to the patient to treat amyloid oligomers. In some examples, the TEMT has a frequency between 1 MHz and 430 THz.

27 Claims, 14 Drawing Sheets

Related U.S. Application Data

(60) Provisional application No. 62/884,513, filed on Aug. 8, 2019.

(51) Int. Cl.
| | | |
|---|---|---|
| *A61N 1/36* | (2006.01) | |
| *A61N 1/378* | (2006.01) | |
| *A61N 5/02* | (2006.01) | |
| *A61N 1/40* | (2006.01) | |
| *A61N 5/06* | (2006.01) | |

(52) U.S. Cl.
CPC .......... *A61N 1/36082* (2013.01); *A61N 1/378* (2013.01); *A61N 1/40* (2013.01); *A61N 5/022* (2013.01); *A61N 2005/0647* (2013.01)

(58) Field of Classification Search
CPC ............ A61N 5/022; A61N 2005/0647; A61N 1/0531; A61N 1/36025; A61N 5/04; A61N 5/0622; A61N 2005/0659
See application file for complete search history.

(56) References Cited

U.S. PATENT DOCUMENTS

| | | | |
|---|---|---|---|
| 6,308,101 | B1 | 10/2001 | Faltys et al. |
| 6,334,069 | B1 | 12/2001 | George |
| 6,410,137 | B1 | 6/2002 | Bunyan |
| 6,463,336 | B1 | 10/2002 | Mawhinney |
| 6,876,337 | B2 | 4/2005 | Larry |
| 7,672,648 | B1 | 3/2010 | Groe |
| 8,535,361 | B2 | 9/2013 | Lim |
| 8,868,177 | B2 | 10/2014 | Simon et al. |
| 9,427,598 | B2 | 8/2016 | Pilla |
| 9,433,797 | B2 | 9/2016 | Pilla |
| 9,672,393 | B1 | 6/2017 | Zhu |
| 10,279,192 | B2 | 5/2019 | Malchano et al. |
| 10,293,177 | B2 | 5/2019 | Malchano et al. |
| 10,307,611 | B2 | 6/2019 | Malchano et al. |
| 11,229,788 | B1 | 1/2022 | John |
| 2004/0122281 | A1 | 6/2004 | Fischell |
| 2004/0127895 | A1 | 7/2004 | Flock |
| 2004/0176805 | A1 | 9/2004 | Whelan |
| 2004/0181115 | A1 | 9/2004 | Sandyk |
| 2004/0199070 | A1 | 10/2004 | Krockel |
| 2005/0228209 | A1 | 10/2005 | Schneider |
| 2007/0244530 | A1 | 10/2007 | Ren |
| 2008/0269851 | A1 | 10/2008 | Deem |
| 2009/0131739 | A1 | 5/2009 | Shalev |
| 2009/0156884 | A1 | 6/2009 | Schneider |
| 2009/0276019 | A1 | 11/2009 | Perez |
| 2010/0042168 | A1 | 2/2010 | Pasche |
| 2010/0114086 | A1 | 5/2010 | Deem |
| 2010/0210894 | A1 | 8/2010 | Pascual-Leone |
| 2011/0230701 | A1 | 9/2011 | Simon |
| 2012/0065456 | A1* | 3/2012 | Arendash ................. A61N 5/02 600/13 |
| 2012/0089201 | A1 | 4/2012 | Pilla |
| 2012/0172954 | A1 | 7/2012 | Zastrow |
| 2012/0283502 | A1* | 11/2012 | Mishelevich .......... A61N 2/006 601/2 |
| 2012/0289869 | A1* | 11/2012 | Tyler ...................... A61B 5/369 601/2 |
| 2013/0237742 | A1 | 9/2013 | Capstick |
| 2014/0187851 | A1 | 7/2014 | Cetroni |
| 2014/0228620 | A1 | 8/2014 | Vasishta |
| 2014/0257017 | A1 | 9/2014 | Arendash et al. |
| 2014/0303425 | A1 | 10/2014 | Pilla |
| 2014/0330353 | A1* | 11/2014 | Knight ............... A61N 1/36025 607/101 |
| 2014/0358199 | A1 | 12/2014 | Lim |
| 2015/0209566 | A1 | 7/2015 | Peyman |
| 2016/0022976 | A1 | 7/2016 | Peyman |
| 2017/0014637 | A1 | 1/2017 | Basser |
| 2017/0246458 | A1 | 8/2017 | Li et al. |
| 2018/0015301 | A1 | 1/2018 | Lim |
| 2018/0043174 | A1 | 2/2018 | Gurfein |
| 2018/0193660 | A1 | 7/2018 | DiMauro et al. |
| 2018/0193664 | A1 | 7/2018 | DiMauro et al. |
| 2019/0030354 | A1 | 1/2019 | Turner |
| 2019/0168013 | A1 | 6/2019 | Arendash et al. |
| 2020/0261737 | A1 | 8/2020 | Neuroem |

FOREIGN PATENT DOCUMENTS

| | | |
|---|---|---|
| CA | 2887843 | 1/2015 |
| CA | 2974891 A1 | 9/2016 |
| CA | 3044440 | 5/2019 |
| CN | 105263575 A | 1/2016 |
| CN | 106413810 A | 2/2017 |
| EP | 1907052 | 1/2010 |
| EP | 1606010 B1 | 2/2012 |
| EP | 2414038 | 2/2012 |
| EP | 3271011 A1 | 1/2018 |
| JP | 2018511371 | 4/2018 |
| KR | 20170129117 A | 11/2017 |
| WO | 2007044386 | 4/2007 |
| WO | 2008141296 | 11/2008 |
| WO | 2015008154 A2 | 1/2015 |
| WO | 2018094226 A1 | 5/2015 |
| WO | 2016151377 A1 | 9/2016 |
| WO | 2018094230 A2 | 5/2018 |
| WO | 2018094232 A1 | 5/2018 |
| WO | 2018132415 A1 | 7/2018 |
| WO | 2018161029 A1 | 9/2018 |
| WO | 2019053625 A1 | 3/2019 |
| WO | 2020102312 A1 | 5/2020 |

OTHER PUBLICATIONS

Gary W. Arendash, "Transcranial Electromagnetic Treatment Against Alzheimber's Disease: Why it has the Potential to Trump Alzheimer's Disease Drug Development," Journal of Alzheimer's Disease, 32 (Jun. 2012) pp. 243-266.

Nguyen, et al; "The Effect of a High Frequency Electromagnetic Field in the Microwave Range on Red Blood Cells"; Sep. 7, 2017.

Karsten, et al; "Red Blood Cells are Dynamic Reservoirs of Cytokines"; Feb. 15, 2018.

Rasouli; "Attenuation of interleukin-1 beta by pulsed electromagnetic fields after traumatic brain injury"; Neuroscience Letters 519 (2012) 4-8.

Merighi; "Signaling pathways involved in anti-inflammatory effects of Pulsed Electromagnetic Field in microglial cells"; Cytokine 125 (2020) 154777.

Peng Lihong et al., The Effect of Pulsed Electromagnetic Fields on Angiogenesis. Bioelectromagnetics, 42: 250-258, 2021, p. 251, col. 1, paragraph 3, col. 2, paragraphs 2-3, p. 254, col. 2, paragraph 2, p. 257, col. 2, paragraph 2.

Das Neves Sofia Pereira et al., CNS-Draining Meningeal Lymphatic Vasculature: Roles, Conundrums and Future Challenges, Frontiers Pharmacology, Apr. 28, 2021, vol. 12, p. 3, col. 1, last paragraph, p. 8, col. 2, last paragraph, p. 9, col. 1, paragraph 1.

Gerstner Elizabeth R. et al., AntiEndothelial Growth Factor Therapy for Malignant Glioma, Curr Neurol Neurosci Rep. May 2009, 9(3):254-262, p. 2, paragraphs 2-3.

* cited by examiner

TRANSCRANIAL ELECTROMAGNETIC TREATMENT

BACKGROUND

Someone in the world develops Alzheimer Disease (AD) every 3 seconds. AD, the most common form of dementia, is a debilitating neuro-degenerative disease in which one experiences confusion, memory impairment, language difficulty, and loss of bodily functions—often becoming fully dependent on others within 4 to 5 years of diagnoses. AD is responsible for 1 in 3 deaths of seniors and kills more people than breast and prostate cancer combined. Today, it is estimated that over 50 million people worldwide are living with AD—the prevalence is rising at an alarming rate and expected to double in the next 30 years.

Pharmaceutical companies have traditionally led the AD research effort, however after tens of billions of dollars in research; AD remains neither preventable, curable, nor even able to be slowed. An effective treatment or cure for AD is estimated to be worth more than $20b per year. Sadly, there are no products on the market that have been proven to cure the disease or even slow disease progression. Other neuro-degenerative diseases and neurological conditions similarly plague society with current treatments and/or cures proving ineffective.

BRIEF DESCRIPTION OF THE DRAWINGS

The accompanying drawings illustrate various examples of the principles described herein and are a part of the specification. The illustrated examples do not limit the scope of the claims.

Figure 1A:
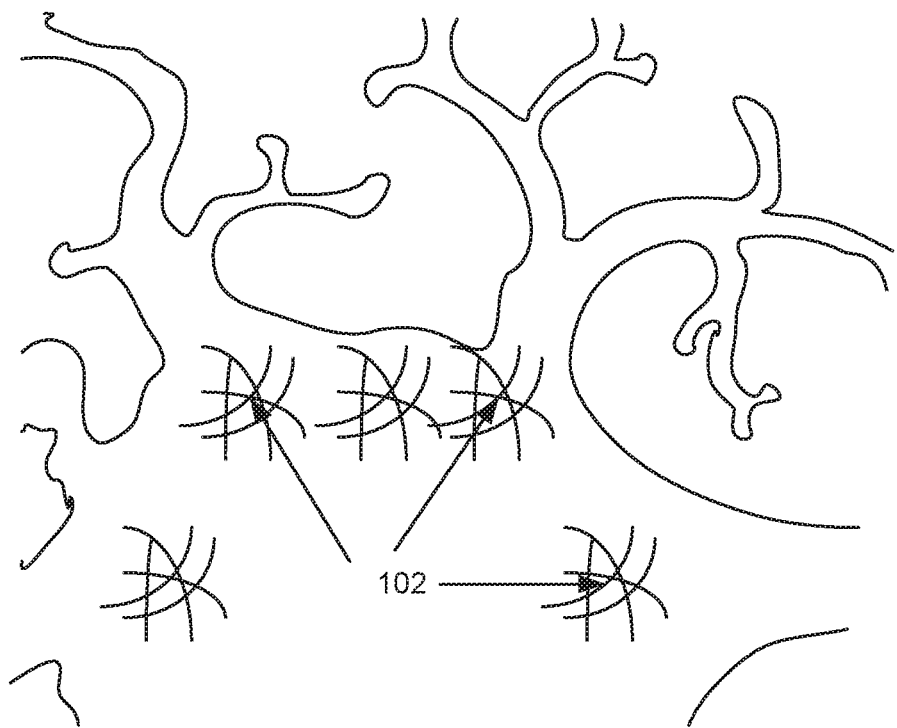
FIGS. 1A and 1B show oligomers before transcranial electromagnetic treatment (TEMT) and disaggregated proteins after TEMT, according to an example of the principles described herein.

Throughout the drawings, identical reference numbers designate similar, but not necessarily identical, elements. The figures are not necessarily to scale, and the size of some parts may be exaggerated or minimized to more clearly illustrate the example shown. The drawings provide examples and/or implementations consistent with the description. However, the description is not limited to the examples and/or implementations shown in the drawings.

DETAILED DESCRIPTION

Alzheimer's Disease (AD) is a neuro-degenerative disease which affects millions of lives and for which no pharmaceutical cure or treatment has been found. Where pharmaceutical solutions have failed, the innovative medical system as described herein, which uses transcranial electromagnetic treatment (TEMT), provides a solution. The system shows unique potential to slow and/or potentially even reverse the effects of AD. The present system includes an array of transmitting emitters connected to a controller, which is communicatively coupled to the transmitting emitters. In some examples, the transmitting emitters are radio wave transmitting antennae, however in other examples the electromagnetic waves may be applied at other frequencies or may be other types of waves entirely. In these other examples, the system may include other components, such as coils or contact patches instead of antennas. The control system may include different components as well and may be placed at different locations on a patient's body. Treatment may be administered in-home by the patient's caregiver rather than through an out-patient facility.

The system of the present specification is the only technology under clinical development that targets both presumed causes of AD—the build-up of small β-amyloid (Aβ) oligomers and tau oligomers within nerve cells. A wide spectrum of pre-clinical studies show that the TEMT system has beneficial cognitive impact linked to disaggregation of toxic protein oligomers (especially Aβ) and brain mitochondrial enhancement in Alzheimer's animal models.

To effectively deliver TEMT to the brain, an efficient emitter or array of emitters should be deployed in a way that balances comfort, cost, and efficacy. As a specific example, each potential patient's head is different in regards to size, hair thickness, and even skull thickness and density. Accordingly, the emitters of the present specification effectively deliver TEMT to brain cells regardless of the individual patient's anatomical makeup.

Accordingly, the present systems, methods, and devices address the above-described problems and others. Specifically, the present systems, methods, and devices provide an efficient and cost-effective delivery of transcranial electromagnetic treatment (TEMT) to the brain cells of a patient regardless of anatomical makeup.

One of the challenges of creating an emitter that is efficient is creating one that directs its energy towards the head and brain (i.e. the target tissue) while minimizing energy leaked away from the head. An additional challenge is to accomplish this while keeping the emitter array small, as directivity gets easier with larger elements at a given frequency. However, having large emitters goes against another desirable characteristic, which is to direct treatments towards specific regions of the brain. These conflicting considerations make it difficult to create an emitter array that provides efficient treatment to specific areas of the brain.

Accordingly, in a first example of the present disclosure, a large single emitter is used to provide treatment to a specific region of the brain. The single emitter may then be moved to the next region when the treatment in the first specific region is completed. In this example, the emitter may be part of a single device that also contains the controller, battery, and signal amplification devices relied on to apply the treatment. In an alternate example, some of these components may be formed on a separate device and connected via cable. In one example, this separate device may be held in place against a treatment surface via a hook and loop strap, although alternate ways to attach the TEMT device exist including elastic or fabric bands or wraps.

In some examples, to indicate a treatment in an area is complete and it is time to move the emitter to the next area, the TEMT system may include a treatment status indicator which may indicate that treatment is done via an audio, visual or tactile indicator. For example, the treatment status indicator may emit a tone when treatment is complete. In another example, the treatment status indicator may activate an on-board vibrator and/or light visible to a caregiver to indicate an end of a treatment. If the device has a speaker for emitting a tone, the device may also play music, audio books, media content, or other audio stimulus during treatment.

In this example, as the embedded emitter is the only item in proximity to the head, as compared to having a total of eight emitters installed, the single emitter can be larger. With a larger emitter, more directionality can be achieved. This is due to the fact that the larger an emitter is relative to the emitted frequency's wavelength, the more directionality can be achieved from that emitter. This allows for a more focused treatment, without as much power loss from radiation going into the air away from the head. The lower the lost power, the less power the device needs to generate, meaning the device may be smaller and lighter.

In another example, a multi-emitter device is implemented in a larger head device that is not worn by the patient, but rather is placed over the patient. That is, the patient may sit under the head device, which is positioned at the proper height to provide effective treatment. The head device includes the electronics to generate the therapy waveforms and the emitters directed towards the patient's head. Such a head device may be constructed to eliminate power radiating away from the patient. In an example, the head unit is positioned over the head of the patient rather like an antique hair dryer.

In both of these examples, the treatment radiated from the emitters may be a continuous waveform that does not vary over the course of the treatment. In another example, the treatment may be a pulsed waveform that, for a particular emitter, switches between radiating and off. In the multi-emitter systems, when one emitter is off, another emitter may be on. This allows for a single therapy waveform generator to be shared by multiple emitters.

In some examples, a single emitter is active at a time. In other examples, several emitters may be active at the same time, either to provide treatment to different areas at the same time, or to have the emitted waveforms combined to produce peaks in particular target areas in the brain. For example, if two emitters are emitting the same frequency, a standing wave pattern is produced, as the two output waves combine to produce both constructive and destructive interference. If the two emitted frequencies are "in-phase", they line up in time and their peaks occur at the same time, which produces a particular standing wave pattern. When the peaks of the signals do not line up, the signals are "out of phase" with each other, and the standing wave pattern changes. With several emitters active, if the phase of the signal between the emitters is varied, the peaks can be moved, and/or steered, to different locations in the brain. In another example, if the power levels of the different signals are changed, this also can move and/or steer the signal to different locations in the brain. When the frequency of the energy from the multiple emitters is the same, the radiation pattern from the emitters produce is in the form of standing waves. Locations of the peaks and nulls of these waves can be calculated, and the locations can be moved by varying the phase of the signal fed to each of the emitters.

In a multi-emitter example, if each emitter was fed by a different frequency, the radiation pattern would be less uniform and a bit more random, since the different frequencies will have varying phases relative to each other. This may produce more of a "random" radiation pattern where the locations of peaks move as the differing frequencies beat against each other. This produces broad coverage, such as steering mechanisms with less complicated circuitry than what is required for phase shifting. The randomness of the radiation pattern can be further varied by changing the difference between the two frequencies, creating a different beat pattern between the two signals.

Since different treatments at different frequencies penetrate the skull and brain differently, the present specification also describes alternating the frequency radiating from an emitter between several set frequencies that are relatively far apart from one another. This facilitates a particular pattern and penetration with one frequency, and a different pattern and penetration for a different frequency. This may also improve treatment effectiveness, as on a biological level there may be a first response to the pulsing of the first frequency, and a second response to the pulsing of the second frequency. With both responses occurring at the same time, treatment efficiency may be increased.

The combination of the two frequencies at different times from a single emitter may also be used to provide for a greater coverage area from that single emitter as compared with a single frequency. This is due to penetration differences between the different frequencies. For example, in a two-emitter system, a first emitter may be radiating at a high frequency while a second emitter radiates at a lower frequency. At some point, the radiating characteristics may switch such that the first emitter is radiating at a low frequency while the second emitter radiates at the high frequency. With this approach, the circuitry that generates the low frequency has its output going to a single emitter and is switched to the appropriate emitter at the correct time. It is the same for the high frequency generator, so that there are always multiple frequencies being generated and distributed to the appropriate emitters. In some examples, if there are enough emitters in the array, a particular frequency could be distributed to multiple emitters at the same time. This may be scaled to more emitters and more frequencies, with a specific example of eight emitters and three frequencies. In this example, the eight emitters provide for sufficient coverage in the certain predetermined locations in the brain, while the three frequencies provide enough of a frequency variation to ensure total penetration and coverage into each of the predetermined locations.

The present specification also describes an emitter array with real time cognitive monitoring during treatments, where feedback can be used to adjust treatment parameters.

For example, if a particular patient is responding better to a particular frequency within the therapy, the treatment may be adjusted to use this favorable frequency more. Alternatively, if the patient shows improvement over testing done over the course of weeks during the treatment, a clinician may adjust the treatment parameters to use more of one particular frequency over another. These treatment adjustments may include frequency, pulse rate, duration, power level, or other parameters of the treatment.

Such cognitive monitoring allows for scalp and hair variations to be accounted for. For example, if a patient has thick hair that increases the distance to the scalp and also has a thicker skull that is harder for the treatment to penetrate, cognitive monitoring would reflect the lower level treatment getting into the brain cells. Despite proper emitter positioning on this particular patient, it may just take higher power to get the same effectiveness of the treatment. Feedback from the monitoring may be used to increase the power out of the emitters. In a different example, treatment frequencies may be lowered as a result of having less cognitive progress. The lower frequencies may provide deeper penetration through the thicker skull and scalp of a particular patient.

In some examples, the cognitive monitoring is done during treatment, or may be performed between treatments at a clinic. If monitoring is performed during the treatment, the TEMT device may have a touchscreen and running interactive games or exercises that would accumulate a performance index that would be tracked over several therapy sessions. One example exercise on a touchscreen would be to display a sequence of numbers followed by showing a numeric keypad and having the patient enter the numbers in order on the keypad. Success would lead to the numeric sequence again being displayed with an additional digit added.

Another example of cognitive monitoring could be performed with buttons and LEDs on the device without the use of a touchscreen. In this example, a memory game could produce a sequence of LED lightings that the patient would mimic with button presses. Each time the sequence was mimicked correctly, the sequence length would be increased by one. The length of the sequence would be the performance measurement for that session. If after a number of sessions, performance does not increase, the device could automatically adjust the treatment parameters.

A further refinement to this process would be to exercise different regions of the brain with different performance games on the device. If it is observed that performance of one region of the brain is increasing less than others, the power level, or other treatment parameters, for the emitter treating that portion of the brain would be adjusted, the treatment time extended, or the parameters otherwise altered.

While emitters have been described that do not come in contact with the scalp and thereby radiate through hair and the scalp, an alternate emitter comes in contact with the skin and induces current through the brain at the treatment frequencies. Due to the skin contact, this emitter does not induce a field onto surrounding cells; instead the emitter conducts electrons to flow through the contact with the skin. In this example, the system/device may include a return emitter to complete the loop for current flow. Accordingly, a full head example may include multiple emitters attached to the skin of the head, where current flows through various emitter pairs to induce current through the brain at the treatment frequency.

In another specific example of the attached emitters, the emitters are installed subcutaneously and operated in pairs the same as with the emitters in contact with the skin. In this example, each emitter may be wired to a control box that may be disconnected between treatments.

In any of the above described examples, the emitters are used to transmit therapy energy into the cells of the brain where they are needed. The brain cells of patients with Alzheimer's and similar diseases suffer from aggregation of toxic proteins from their singular (non-toxic) form to small self-aggregated oligomers. This self-aggregation process starts with the single/monomeric form of the protein A-beta (Aβ) self-aggregating into oligomers, which induces the oligomerization of a second toxic protein (tau). Both oligomers are toxic to neurons, causing their dysfunction and eventual death. The monomeric units with any given small oligomers of Aβ and tau are held together by weak ionic attraction via hydrogen bonding. Mounting evidence suggests that TEMT disaggregates these toxic protein oligomers through a destabilization of H-bonds between oligomer monomers via dipole-dipole interactions, vibration, and/or resonance phenomena. The treatment waves provide a field that the polarized molecules align with. The force that polarizes the molecules is stronger than the strength of the H-bonds, so the result is that the H-bonds are broken.

In this regard, electromagnetic-waves, for examples those in the radio frequency range have been shown to cause reduced dipole-dipole interactions (dielectric loss), which leads to a decrease in inter-molecular H-bonding. Indeed, the toxic protein β-sheet aggregates of Aβ, tau, and α-synuclein have a common backbone polarization that is stabilized via "two-electron" interactions of H-bonds—a backbone that appears to be selectively disrupted by radio frequency waves. Once these toxic oligomers are transformed into monomers and dimers, they are subsequently removed from the brain through circulating cerebrospinal fluid (CSF). This mechanism of toxic protein disaggregation, which happens inside brain cells, cannot be achieved with pharmaceuticals, as the brain protects its cells from chemicals that are in the blood stream. In contrast, electromagnetic energy can penetrate cell walls and influence these protein aggregates inside the cells independent of the blood-brain barrier.

It will be evident to those skilled in the art that variations in implementation of these schemes, including alternate detection mechanisms and other implementation details, will still be included in the overall principles described as part of this invention.

Among other examples, the present specification describes a method. According to the method, an emitter of a transcranial electromagnetic treatment (TEMT) system is positioned at a location relative to a head of a patient such that the emitter emits an electromagnetic frequency signal toward the head of the patient. The emitter is activated to apply transcranial electromagnetic treatment (TEMT) to the patient to disaggregate amyloid oligomers.

The present specification also describes another method disaggregating amyloid oligomers. In this example, an emitter of a transcranial electromagnetic treatment (TEMT) system is positioned at a first location relative to a head of a patient. The emitter is activated to apply transcranial TEMT with the emitter at the first location to disaggregate at least one of Aβ and tau oligomers. The emitter is repositioned to a second location relative to the head of the patient. The directional emitter is again activated to apply TEMT at the second location to disaggregate at least one of Aβ and tau oligomers.

The present specification also describes a TEMT system. The TEMT system includes a head device to be placed over a patient. The TEMT system also includes an emitter array disposed in the head device. The emitter array is to be positioned over a head of a patient and includes a plurality of emitters. The TEMT system also includes a controller to control the emission of radiation from each of the emitters.

In another example, the TEMT system includes an array of emitters including at least a first emitter and a second emitter. The first emitter and the second emitter are positioned to direct electromagnetic frequency signals toward the same, or different, brain area of a patient. A controller of the system simultaneously directs the first emitter to broadcast a first signal frequency toward the brain area of the patient and direct the second emitter to broadcast a second, different, signal frequency toward the same/different brain of the patient.

In another example, the present specification describes a method of administering transcranial electromagnetic treatment (TEMT). According to the method, a first signal is directed toward a brain of a patient from a first emitter wherein the first signal has a frequency of between 1 MHz and 3 GHz. A second signal is directed toward the brain of the patient from the first emitter. In this example, the second signal has a frequency between 1 MHz and 3 GHz and the second frequency differs from the first frequency.

In another example, the TEMT system includes a first emitter in electrical contact with a scalp of a patient. The system also includes a controller to cause the first emitter to emit a signal with a frequency between 1 MHz and 430 THz.

In another example, the TEMT system includes a subcutaneous implant comprising a controller and an emitter to emit a signal with a frequency between 1 MHz and 430 THz. The signal is directed toward a brain of a patient with the subcutaneous implant. The system also includes a power source to provide power to the subcutaneous implant.

In yet another example, a first frequency is applied to a brain region of a patient using TEMT. A second frequency is simultaneously applied to the either the same or different brain region of the patient using TEMT. The second frequency is varied with regards to the first frequency.

Figure 1B:
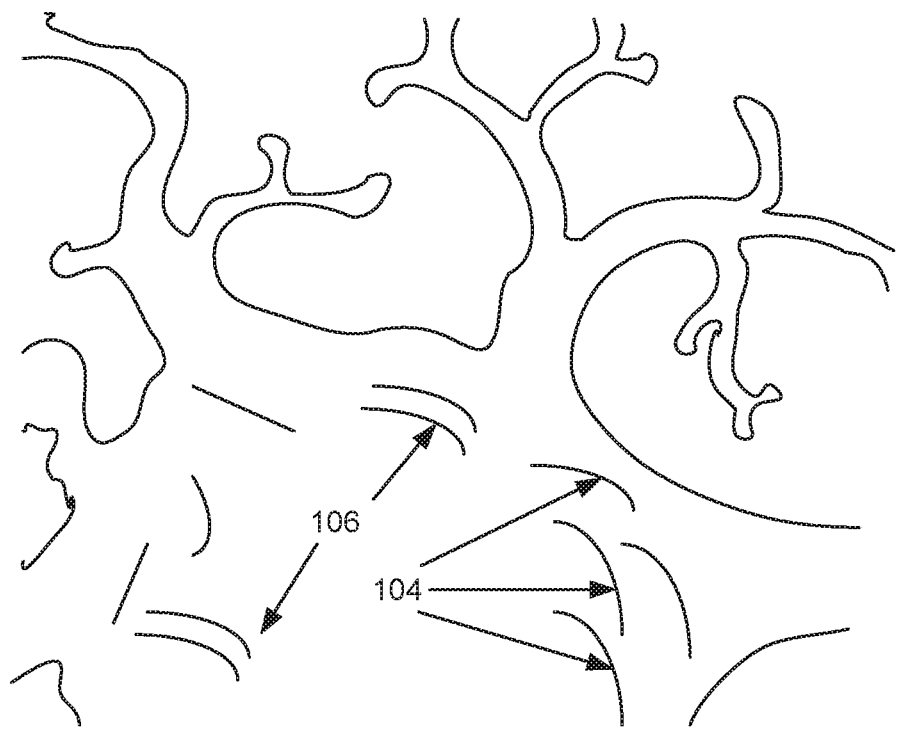

Turning now to the figures, FIGS. 1A and 1B show oligomers before TEMT and disaggregated proteins after TEMT, according to an example of the principles described herein. Specifically, FIG. 1A depicts protein molecules aggregated as oligomers (102) before TEMT treatment. That is, before treatment, naturally occurring oligomers (102) form over time. This occurs as the molecules are attracted to each other due to their ionic nature, and are held together by hydrogen bonds. FIG. 1B shows disaggregated protein molecules. That is, after treatment, individual non-aggregated molecules are characterized as monomers (104) and dimers (106). Once the molecules are organized in this way, their destructive effects within the brain cells are reduced and/or eliminated. In FIGS. 1A and 1B, the oligomers, monomers, and dimers in this figure represent Aβ oligomers/monomers/dimers or tau oligomers/monomers/dimers.

Figure 2:
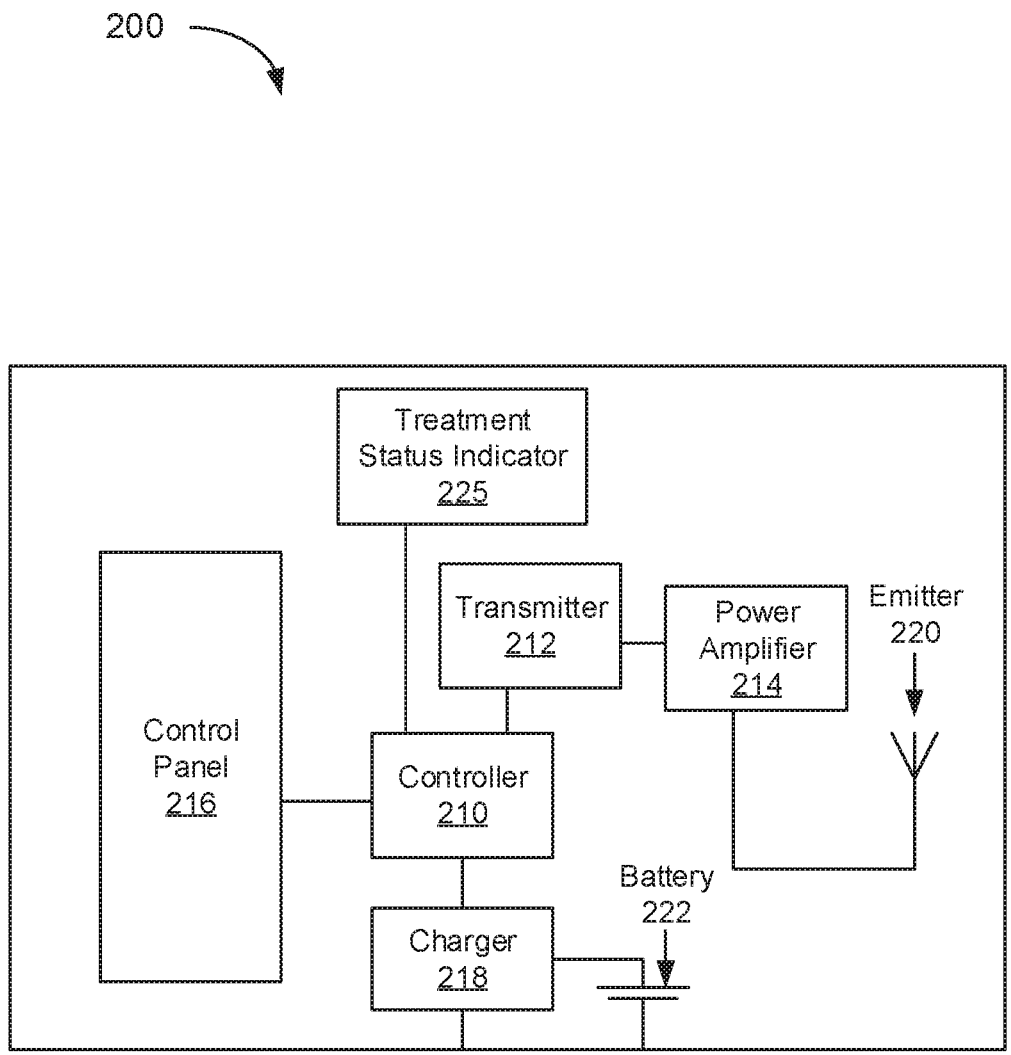
FIG. 2 is a diagram of a single emitter TEMT system, according to an example of the principles described herein.

FIG. 2 is a diagram of a single emitter TEMT system (200), according to an example of the principles described herein. In this example, the TEMT system (200) includes of a single emitter (220) and controller (210) packaged together. Such a TEMT system (200) may be used by the patient receiving treatment. During such a treatment, the TEMT system (200) is held against the patient at the treatment location. In some examples, the TEMT system (200) may be held in place with a strap, cord, elastic, and/or similar mechanism. The TEMT system (200) provides the desired TEMT to the neurons to prevent and/or reverse formation of amyloid oligomers and/or tau oligomers. In some examples, the TEMT system (200) may be connected to an AC-DC adapter for charging. In other examples, the TEMT system (200) does not have a battery and battery charger and is instead supplied constant power by the AC-DC adapter.

The TEMT system (200) includes a controller (210) which manages the treatments, schedules, and user interface. For example, during a treatment, the controller (210) directs the transmitter (212) to generate and amplify the electromagnetic frequency (EMF) waveforms according to treatment parameters. More specifically, in some examples, the electromagnetic frequency signals may be radio-frequency signals.

The power amplifier (PA) (214) amplifies the EMF signal to the levels indicated by the treatment parameters. The PA (214) output is fed into the emitter (220), which transfers the treatment to the patient. The control panel (216) provides the interface to the user, and may be used to start or stop treatments, and to provide feedback and information to the user, such as treatment status and battery level. Additionally, cognitive monitoring, which is described in more detail below, may be implemented on the control panel (216) in the form of a memory game. In one particular example, the memory game may require the repeat of a sequence or other memory exercises and tests.

The controller (210) may activate the emitter (220) for different periods of time. For example, the controller (210) may activate the emitter (220) for 5 minutes, 10 minutes, 15 minutes, 30 minutes, 60 minutes, 120 minutes, or any other period of time. During such a time period, the emitters (220) may deliver between 0.1 W/kg and 8.0 W/kg average SAR. In some examples, the activation of the emitter (220) may be defined by the frequency of the emitted signal. For example, the emitter (220) may emit a signal with a frequency between 1 MHz and 430 THz.

The activation period may be determined based on delivering the electromagnetic energy at a safe level, and assuring enough energy is delivered to disrupt oligomer consolidation in the neurons. The activation period may also be selected based on a number of sessions expected in a given period of time. For example, TEMT may be applied daily for a time period of at least 2 days. For example, if the emitter (220) is to be relocated between sessions then a set of four 10-minute sessions may provide adequate daily treatment for a patient. In some examples, it may be useful to have fewer, longer sessions to encourage patient acceptance of the treatment. In other examples, a greater number of short sessions may provide better coverage compared with fewer, longer sessions.

In some examples, the transmitter (212) may generate a continuous signal. In this example, the SAR level of each emitter (220) may be reduced so that all emitters (220) do not collectively generate more than a predetermined amount of power. In other examples, the transmitter (212) may generate a pulsed signal. Still further in some examples, the transmitter (212) may alternate between multiple frequencies. For example, the transmitter (112) may first provide a higher frequency and then provide a second, lower frequency. The use of multiple frequencies increases the coverage as different frequencies have different penetrating power resulting in different coverage areas relative to the emitter (220).

As described above, the power amplifier (214) increases the power of the signal generated by the transmitter (212) and provides the powered signal to the emitter (220) for transmission toward the target tissue. In some examples, the power amplifier (214) may be integrated with the transmitter (212).

As described above, the use of a single emitter (220) in the TEMT device (200) allows for a larger emitter (220) and allows for greater directionality to the emitted waveform compared with multiple smaller emitters, for example, as described with respect to FIG. 2, below. In some examples, the emitter (220) is not in electrical contact with the patient's skin. In this example, an electric field is generated to disrupt the hydrogen bonding in the oligomers in the neurons of the patient's brain.

The control panel (216) allows a user to interact with the controller (210) and control the functioning of the TEMT system (200). For example, the control panel (216) may include a security mechanism to limit control of the device to authorized user(s). The control panel (216) may display various pieces of information including session information, the location of the emitter relative to the brain, a power level for the battery (222) and/or prompt recharging of the battery (222) by a user.

In some examples, a charger (218) may be included in the TEMT device (200) to facilitate recharging of the battery (222). The battery (222) powers the TEMT system (200) during treatment. In some examples, the battery (222) may be recharged between treatment sessions. Between treatments, the TEMT system (200) may be connected to a power source for charging of the internal battery (222). When, the TEMT device (200) is coupled to an AC-DC adapter, the charger (218) charges the battery (222). During treatment, the TEMT system (200) may be decoupled from the power source. In some examples, controller (210) gets charge status and AC-DC adapter presence from the charger (218) and displays status on the control panel (216).

Figure 6:
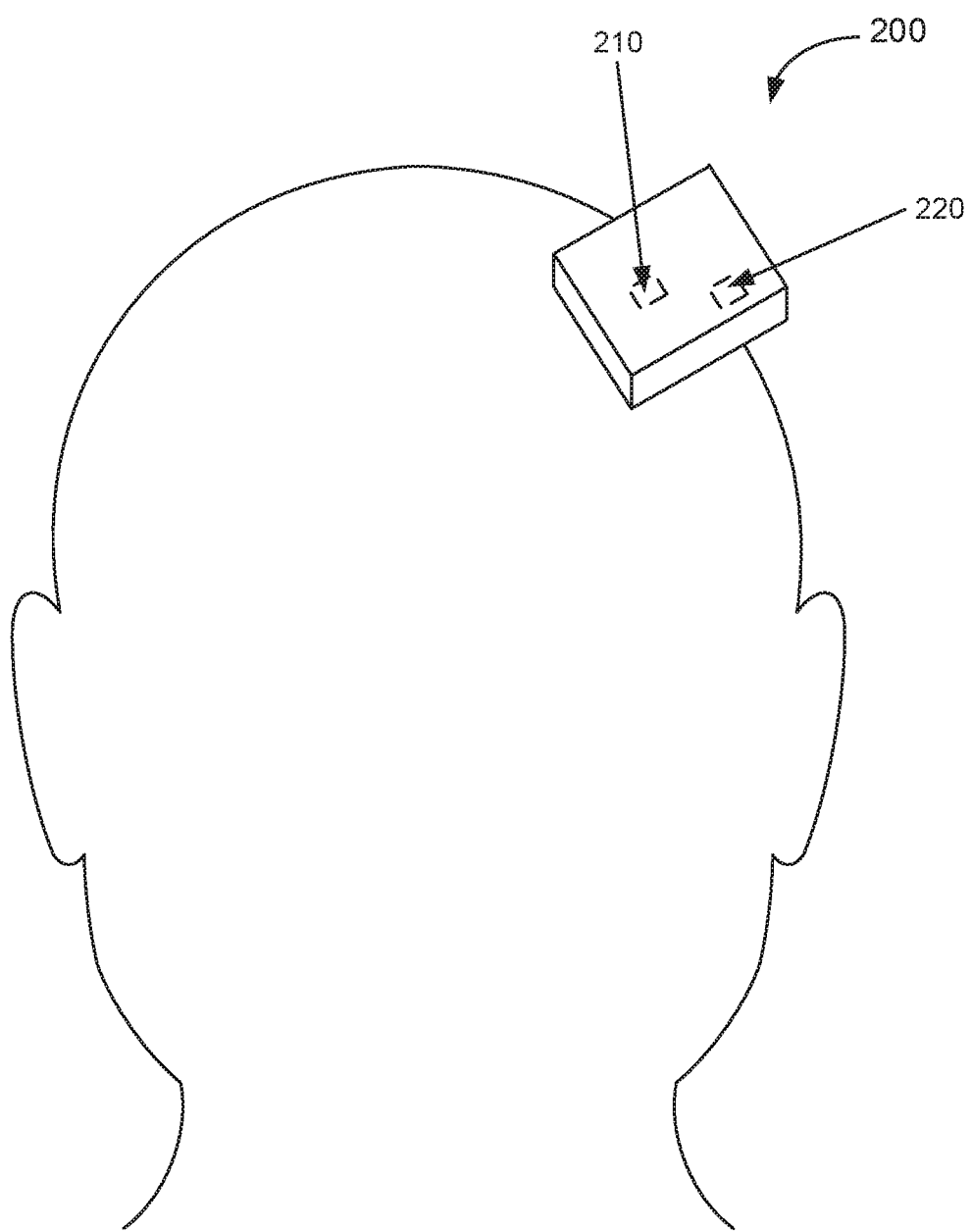
FIG. 6 depicts a portable TEMT system on a patient's head, according to an example of the principles described herein.

In the example depicted in FIG. 2, the TEMT system (200) also includes a treatment status indicator (225) to indicate a status of the treatment. For example, an indicator such as an audio, visual, or tactile indicator may provide an indication of when a particular treatment session is complete. In the case of a portable or handheld TEMT system (200) as depicted in FIG. 6, such an indicator may cue the caregiver to move the portable TEMT system (200).

Figure 3:
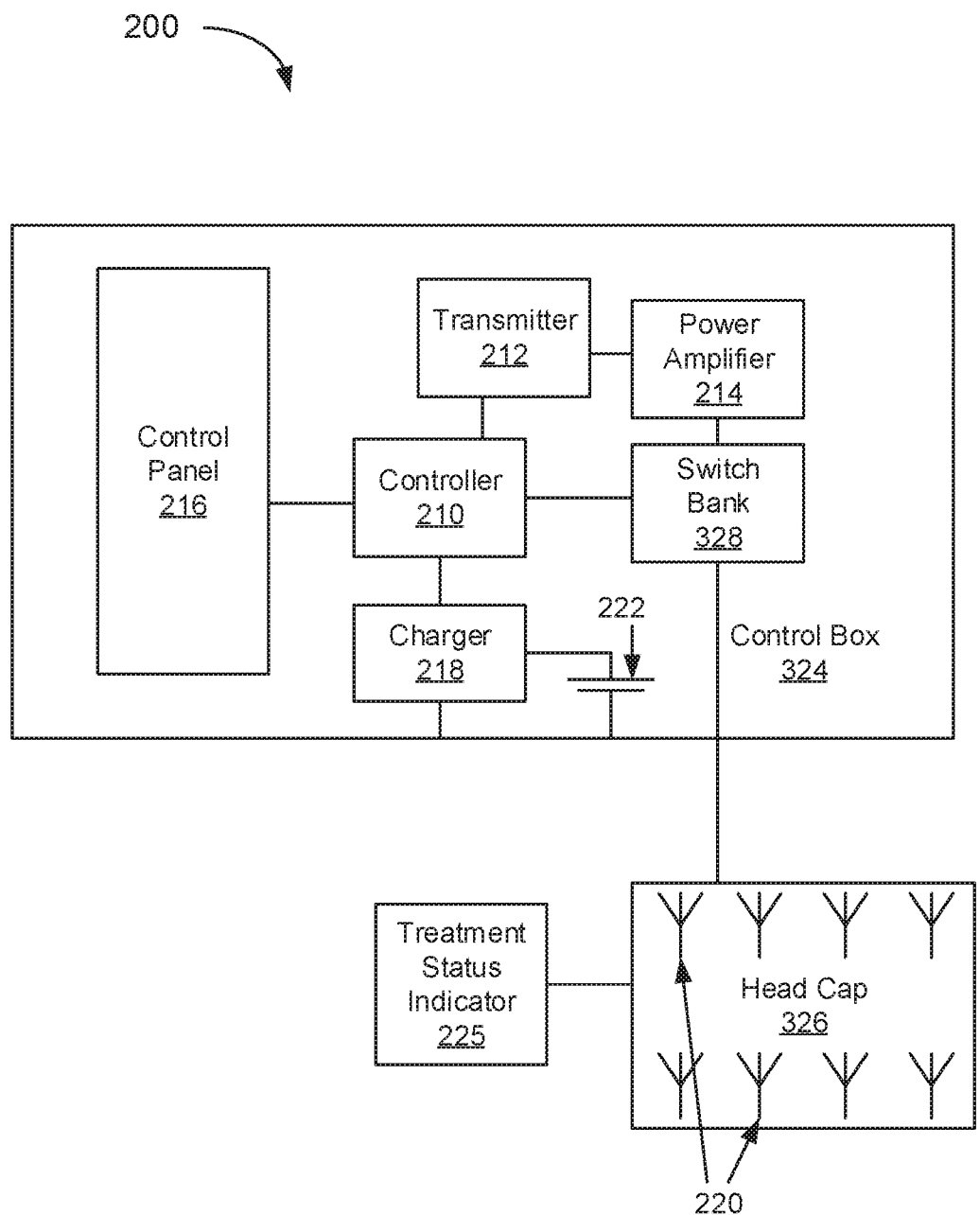
FIG. 3 is a diagram of an eight emitter TEMT system with a cabled head cap, according to an example of the principles described herein.

FIG. 3 is a diagram of an eight emitter (220) TEMT system (200) with a cabled head cap (326), according to an example of the principles described herein. While FIG. 3 depicts eight emitters (220), the TEMT system (200) may include any number of emitters including between 1 and 100. Specifically, FIG. 3 depicts the control box (324) that drives an array of eight emitters (220) in a head cap (326) worn by a patient receiving treatment. During a treatment, the head cap (326) is worn by the patient. The control box (324), which includes the controller (210) and other components, may be attached to the patient's arm, for example with a hook and loop fastener or similar strap. In another example, the control box (324) may be held in a pouch that can be attached to a shoulder strap or belt. As described above, between treatments, the control box (324) may be connected to an AC-DC adapter for charging. This allows the internal battery (222) to be recharged.

The control box (324) includes the controller (210), transmitter (212), power amplifier (214), control panel (216), charger (218), and battery (222) as described above in connection with FIG. 2. In the example depicted in FIG. 3, the control box (324) includes a switch bank (328) which enables the use of multiple emitters (220) operating with a common signal provided by the power amplifier (214). In an alternate example, the switch bank (328) may be located in the head cap (326).

During use, the head cap (326) is placed on a patient's head which brings the emitters (220) into proximity to the patient. In some examples, the head cap (326) may include a radio absorbing liner to help reduce the amount of stray RF energy emitted from the emitters (220). The head cap (326) may be adjustable to accommodate different sized heads.

As in the example depicted in FIG. 2, the TEMT system (200) also includes a treatment status indicator (225) to indicate a status of the treatment.

Figure 4:
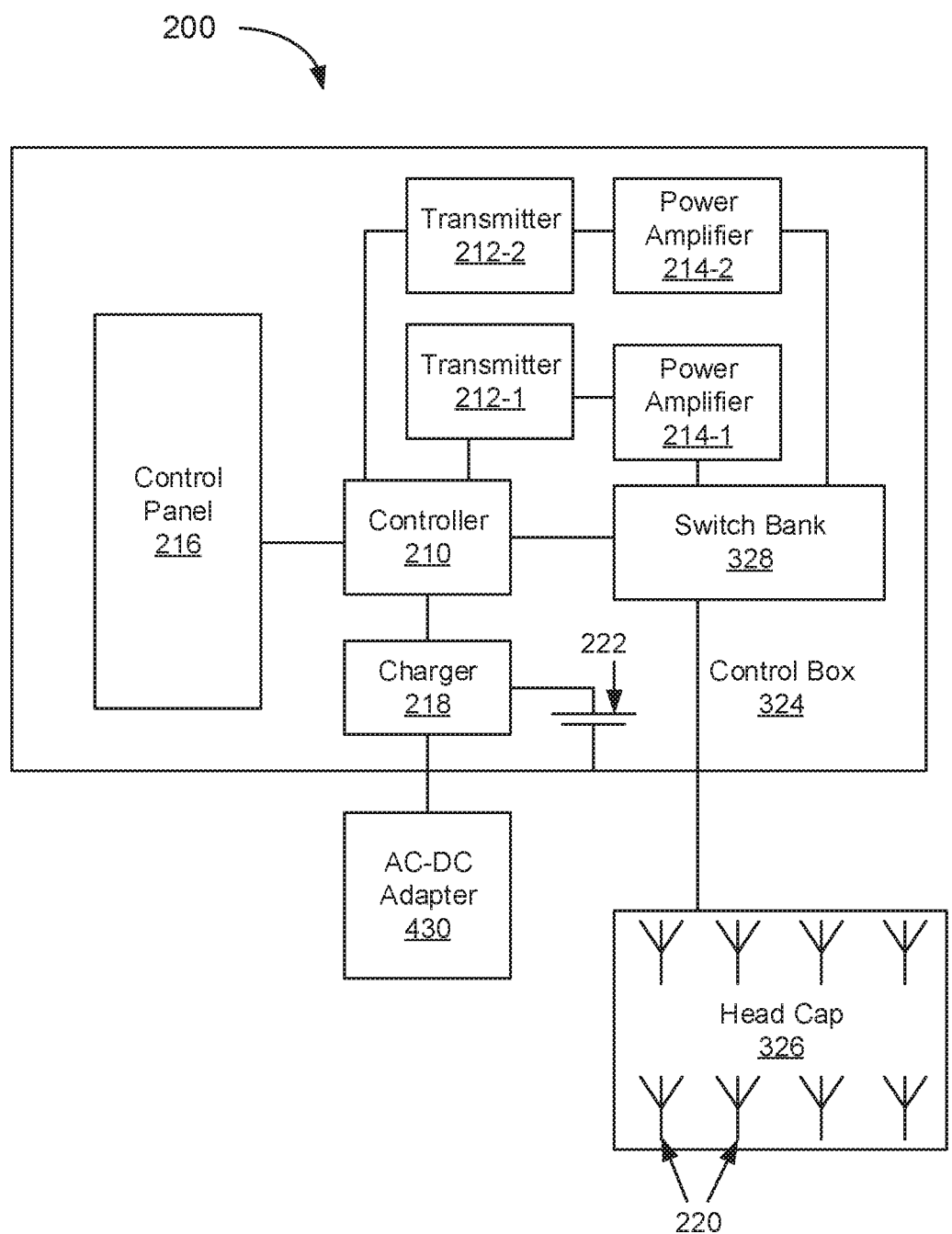
FIG. 4 is a diagram of an eight emitter two-frequency TEMT system with a cabled head cap, according to an example of the principles described herein.

FIG. 4 is a diagram of an eight emitter (220) two-frequency TEMT system (200) with a cabled head cap (326), according to an example of the principles described herein. Specifically, FIG. 4 depicts the control box (324) that drives an array of eight emitters (220) in a head cap (326) worn by a patient receiving treatment. Such a two-frequency TEMT system (200) has the ability to generate both low and high frequency therapy signals, and each emitter (220) can either be applying a first low frequency, a second high frequency, or be in an idle mode. FIG. 4 also depicts the AC-DC adapter (430) that is plugged into the wall and used for charging.

The control box (324) includes the controller (210), charger (218), battery (222), and control panel (216) as described above. In this example, the controller (210) enables both the low frequency transmitter (212-1) and the high frequency transmitter (212-2) to generate the necessary RF waveforms as per the treatment parameters. The respective PAs (214-1, 214-2) then amplify the RF signals to the levels proscribed for treatment. The output of the low frequency PA (214-1) and the high frequency PA (214-2) are fed into the switch bank (328), which directs the EMF, and more specifically RF, signals to the appropriate emitters (220) within the emitter (220) array located in the head cap (326).

The controller (210) and switch bank (328) may also be configured to provide different frequencies to different emitters (220). For example, a low frequency may always be applied to a first emitter, while a high frequency may always be applied to a second emitter. The lower frequency may better penetrate the skull and scalp of a particular portion of the head, and may be a preferred frequency for a particular emitter serving a particular portion of the head. Extending this, every emitter in the TEMT device may use its own unique frequency that is optimized for that portion of the head.

In some examples, the switch bank (328) may have a purely switching function, may control power, and may also control the phase to the different emitters in the emitter (220) array. In its switching function, the switch bank (328) takes the two input signals and can apply either signal onto any of the outputs, therefore onto any of the emitters (220) within the array. The switch bank (328) can also apply one of its inputs to many of the emitters (220) in the array.

Figure 5:
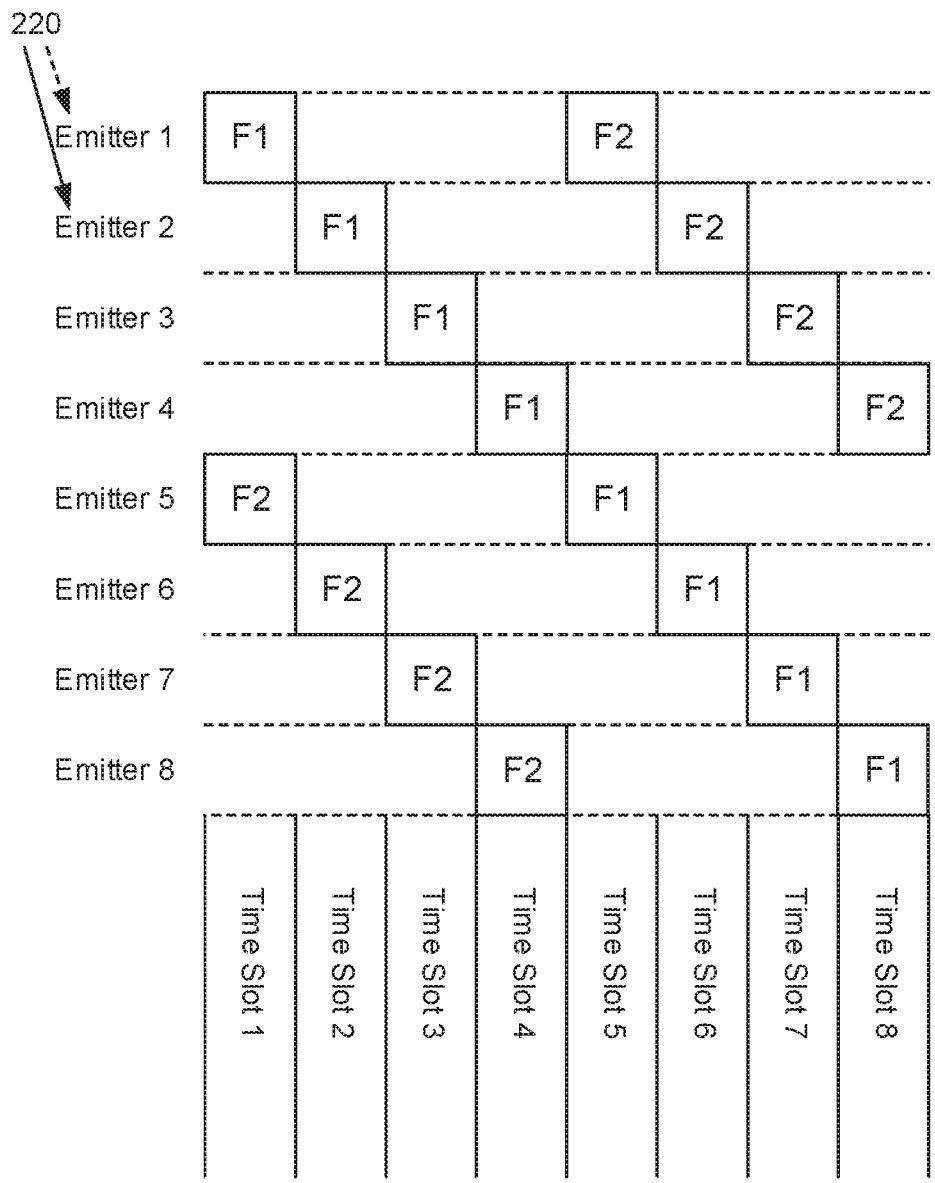
FIG. 5 depicts a treatment pattern of an eight emitter two-frequency TEMT system, according to an example of the principles described herein.

FIG. 5 depicts a treatment pattern of an eight emitter (FIG. 2, 220) two-frequency TEMT system (FIG. 2, 200), according to an example of the principles described herein. Since there are 2 transmitters (FIG. 2, 212-1, 212-2), there are both low and high frequency outputs as depicted in FIG. 5. In FIG. 5, time progresses from left to right and each labeled time slot is an amount of time that the device is configured with the shown treatment outputs. Time Slot 1 shows Emitter 1 outputting a high frequency treatment (F1) and Emitter 5 outputting a low frequency treatment (F2). The next time slot shows both treatment outputs moving to the next emitter (FIG. 2, 220). The frequencies shift this way through all of the emitters (FIG. 2, 220) of the array.

This treatment therapy can be understood by focusing on a single emitter (FIG. 2, 220) and what it outputs over time. Consider as an example Emitter 5. It outputs a low frequency therapy for one slot, then is idle for 3 time slots, then outputs a high frequency therapy, then is idle for 3 time slots, before repeating the low frequency therapy (after slot 8 the pattern starts over again with slot 1). Notice that each emitter (FIG. 2, 220) follows the same pattern of Low/3 idle/High/3 idle, so each pattern is just shifted in time. That is, a first signal emitted by a first emitter (FIG. 2, 220), Emitter 1, and a second signal emitted by a second emitter (FIG. 2, 220), Emitter 2, are the same, but time-shifted relative to one another. Therefore, each location of the brain is getting the same treatment pattern, just offset in time from other locations.

While FIG. 5 depicts one example, other examples may be implemented. For example, the treatment may include just a single frequency, more than 2 frequencies, a different number of emitters, or any variations in the patterns over time. In one example, one frequency is a random and/or noise signal and the other frequency is a continuous signal at a fixed frequency. In some examples, the pairs of emitters (FIG. 2, 220) active at a given time are located opposite each other so as to maximize coverage of the brain.

FIG. 6 depicts a portable TEMT system (200) on a patient's head, according to an example of the principles described herein. Specifically, in this example, the TEMT system (200) is a handheld or portable device that includes the controller (210) and the emitter (220). In FIG. 6, the controller (210) and emitter (220) are indicated in dash to indicate their position internal to the handheld device. While FIG. 6 depicts the controller (210) and emitter (220) in a single device, in some examples, the handheld device just includes the emitter (220) and a second device includes the controller (210). In this example, the second device is coupled, via a cable or other communication channel, to the handheld device.

In this example, the TEMT system (200) is placed on the head to provide a treatment at a specific location, and then is moved to a subsequent location to provide the next treatment. As descried above, the TEMT system (200) may indicate that treatment at a particular location is complete through audio, visual, and tactile indicators. Upon moving the TEMT system (200) to a new location on the head, the user may press a button on the device to start treatment on the new location.

In some examples, the TEMT system (200) is held in place with a strap, such as a hook and loop fastener, an elastic strap, a fabric strap or a strap formed of another material. In some examples, the TEMT system (200) may be held in place by multiple straps connected together in a harness format that would locate the TEMT system (200) and keep it from sliding to a different position. In this example, the harness may use fixed points on the head, such as ears and/or chin, for proper location and prevention of sliding or rotating. In some examples, the TEMT system (200) may provide a visual indication of battery life to ensure enough battery is available before a new treatment is started.

Figure 7:
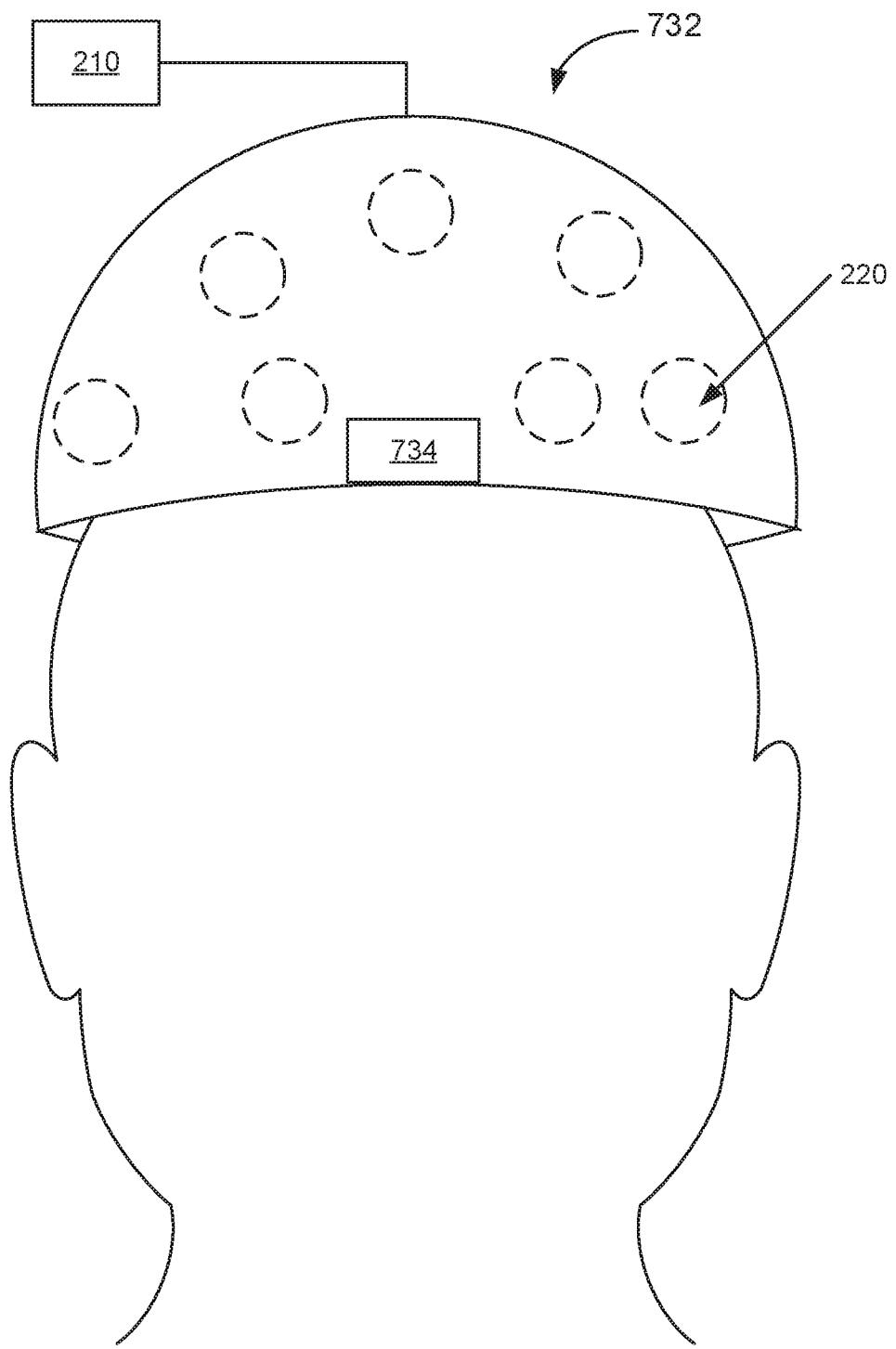
FIG. 7 depicts a TEMT system with a head device with multiple emitters that a patient sits under, according to an example of the principles described herein.

FIG. 7 depicts a head device (732) with multiple emitters (220) that a patient sits under, according to an example of the principles described herein. For simplicity, in FIG. 7 just one emitter (220) is indicated with a reference number. The emitters (220) are indicated in dash to indicate their position on an inside of the head device (732). Before the treatment begins, the patient sits under the head device (732), which is placed over the patient. The head device (732) may be lowered relative to a patient, such that the patient's head is surrounded. As shown in FIG. 7, the head device (732) has not been fully lowered to fully engulf the patient's upper head. Once lowered, the emitter (220) array disposed in the head device (732) is positioned over a head of the patient.

In some examples, the head device (732) may be oversized to allow for the largest of patient heads. When a patient with a smaller head is using the head device (732), there may be a larger gap between the head unit (732) and the patient's head. The larger gap may mean that less power from the emitters (220) will fall incident to the head because of the propagation loss over the larger distance. To offset this, the head device (732) may transmit higher power levels through the further away emitters (220).

Accordingly, the head device (732) may include a distance sensor (734) to determine a distance between the head device (732) and the head of the patient. In this example, the controller (210) which may be integrated with the head unit (732) or separate, receives an output of the distance sensor (734) and modifies treatment parameters. For example, the emitter (220) power may be increased to offset the distance to provide the correct power levels falling incident to the head. Because measured distance is to the scalp, this example may reduce the impact of variations in patients' hair thicknesses and styles, and the treatment power that falls incident to the scalp is the same across patients regardless of hair thickness. Because the head device (732) need not be secured to the patient during the treatment, this distance monitoring and power adjustment continues through the course of the treatment. This continuous monitoring allows corrections to be made as the patient moves around within the head device (732) during the treatment session.

As the patient moves around under the head device (732), alignment between each of the emitters (220) and the location each is targeting in the head might be lost. Accordingly, the present head device (732) may account for such an alignment issue.

In one example, an inner layer of the head device (732) may include the emitters (220). This inner layer may be moved by motors to track the rotation and tilt of the patient's head. Sensors, including a combination of the distance sensor (734) and/or imaging sensors may be used to detect the position of the patient's head. As the head moves, the head device (732) activates the motors to move the inner layer to follow the patient's head.

In another example, more emitters (220) may be in the head device (732) than are needed to apply a therapy. As the patient's head movements are detected, emitters (220) that align with the target locations of the head are used for applying the therapy and other emitters (220) are disabled.

In yet another example, the head device (732) may include a flexible inner layer. After a patient is sitting under the head device (732) and the head device (732) is lowered on the patient, draw strings may be pulled that tighten the flexible inner layer to the patient's head. During this process, the patient's head should be oriented in a known position that provides proper alignment. Once the inner layer is drawn to the head, it is secured as a cap and follows the movements of the patient's head. A chin strap or other additional securing mechanism may be used to secure the flexible inner layer to the patient's head. In this example, the patient may receive treatment in a clinic where they may be monitored by an industry professional.

In some examples, the head device (732) may include directional emitters (220) that are focused towards the head. In this example, an outer layer of the head device (732) helps direct energy towards the head and minimizes leakage away from the patient.

As described above, in some examples, the head device (732) may have a built-in controller (210) and power source such that necessary components are entirely integrated into the head device (732). As described above, the power source can be a battery (FIG. 2, 222) or a connection to a wall socket. In some examples, the head device (732) may include a button to start treatment, and an indication that the treatment session is complete. In one application, this head device (732) could be more advanced and offer more treatment options compared to an in-home device. Thus, the patient/subject may come to a clinic periodically to receive this more advanced treatment provided by such a clinically-based head device (732).

Figure 8A:
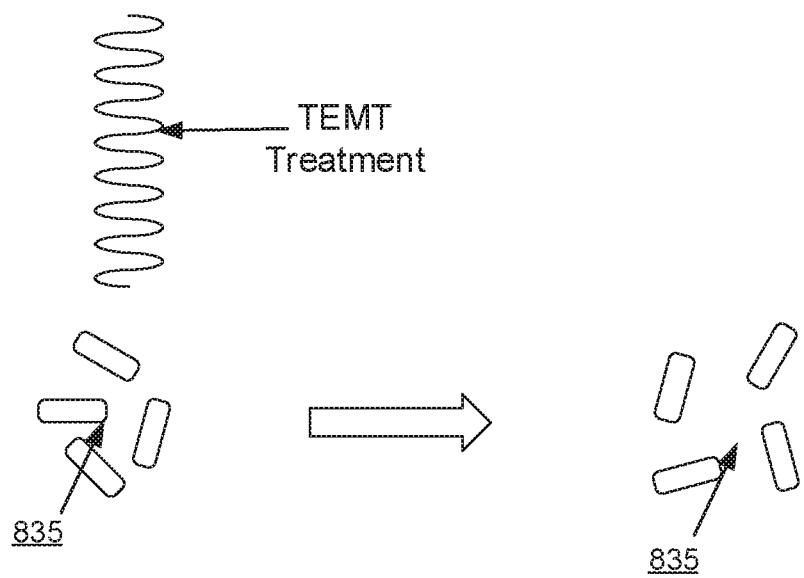
FIGS. 8A and 8B depict A-beta (An) and tau oligomers forming and how electromagnetic frequency disaggregates them, according to an example of the principles described herein.
Figure 8B:
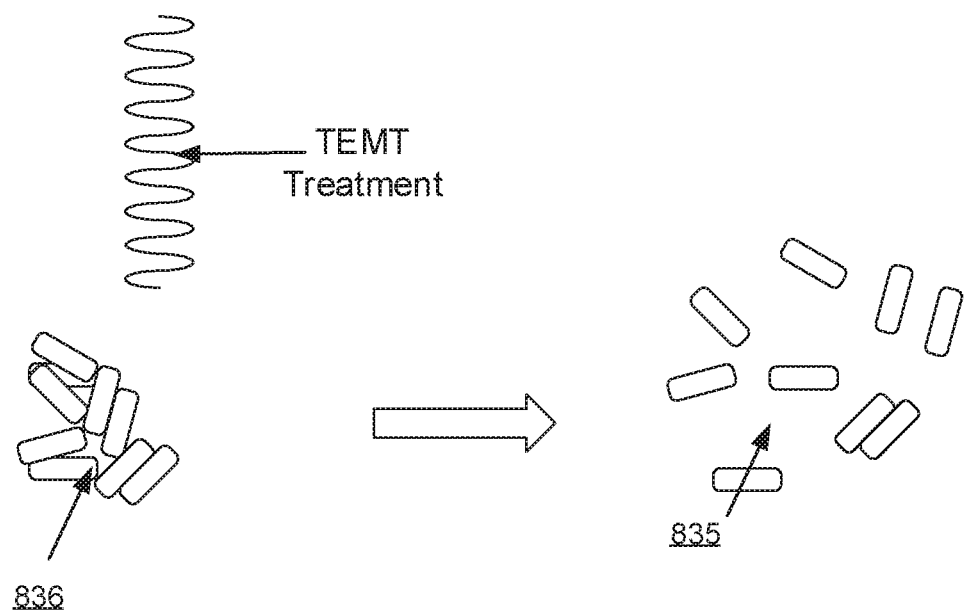

FIGS. 8A and 8B depict Aβ and tau oligomers forming and how electromagnetic frequency disaggregates them, according to an example of the principles described herein. Specifically, in FIG. 8A, the proteins (835) as found in a healthy brain cell may be not yet aggregated. Over time they may gather and form oligomers (836) as depicted in FIG. 8B, but are treated with TEMT which prevents the formation of oligomers (836). As a result, the proteins remain as disaggregated proteins (835).

In FIG. 8B, the agglomerated proteins, or oligomers (836) are treated with TEMT. The TEMT disrupts the hydrogen bonds between the aggregated proteins causing them to revert to disaggregated proteins (835) such as monomers and dimers. The monomers and dimers may then be used or excreted by the neuron into the spinal fluid (CSF).

In other words, TEMT disrupts the attractions between the proteins of the oligomers providing energy to disaggregate the oligomer structures in the neurons. TEMT is believed to treat toxic Aβ and tau oligomer formation by 1) disrupting the formation of both Aβ and tau oligomers and 2) disaggregating both Aβ and tau oligomers into monomers and dimers. The monomers and dimers may be handled by the cell's normal processes, including excretion if present in excess amounts.

Figure 9:
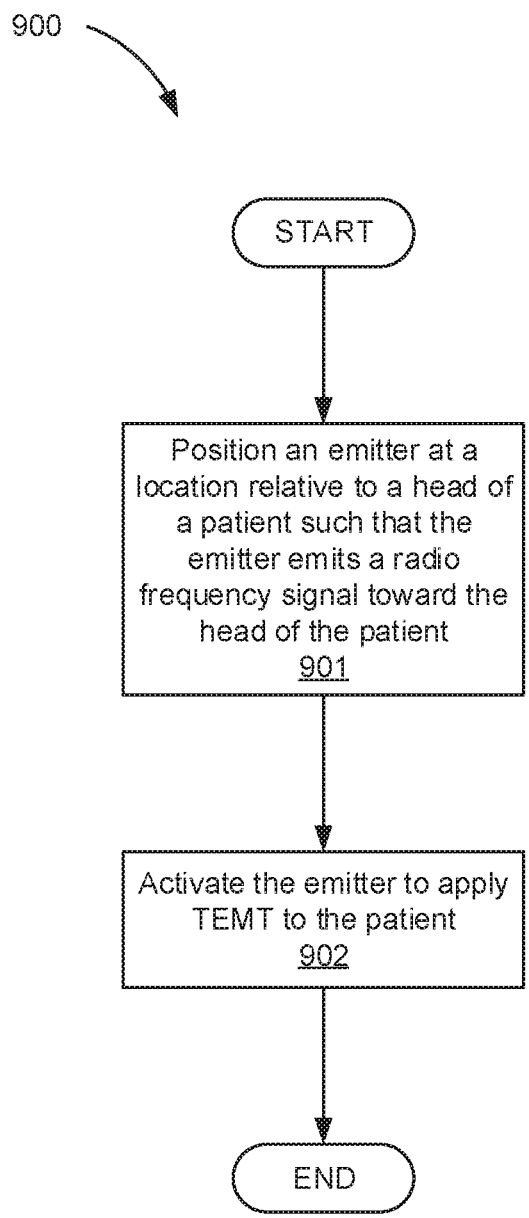
FIG. 9 is a method for transcranial electromagnetic treatment (TEMT), according to an example of the principles described herein.

FIG. 9 is a flowchart for a method (900) for transcranial electromagnetic treatment (TEMT), according to an example of the principles described herein. According to the method (900), an emitter (FIG. 2, 220) of a TEMT system (FIG. 2, 200) is positioned (block 901) at a location relative to a head of a patient such that the emitter (FIG. 2, 220) emits an electromagnetic, and in some examples a radio, frequency signal toward the head of the patient. In some examples, the emitter (FIG. 2, 220) may be located in a head cap (326), in a portable treatment unit as depicted in FIG. 2 or in a head device (FIG. 7, 732). In any of these examples, the emitter (FIG. 2, 220) may be part of an array of emitters. In some examples, the emitter (FIG. 2, 220) may be proximate the skin and in some particular examples may even be in contact with the skin of the patient.

The emitter (FIG. 2, 220) or emitters (FIG. 2, 220) are activated (block 902) to apply transcranial electromagnetic treatment (TEMT). In some examples, the TEMT may have a specific absorbance from 0.1 to 8.0 W/kg and may be applied with a frequency of 1 MHz to 430 THz. More specifically, the emitters may emit at a frequency of between 1 MHz and 3 GHz and even more particularly in a range of 902 to 928 MHz. In some examples, the TEMT is applied in an Industrial, Scientific, Medical (ISM) band of radio frequencies. As a particular example, the emitters (FIG. 2, 220) may emit at a frequency of between 1 MHz to 3 GHz, having a pulse repetition rate of 10 Hz to 300 Hz and a duty cycle of between 1% and 100%

As described above, in some examples, the emitters (FIG. 2, 220) may alternate between two or more frequencies. In a specific example, the TEMT is applied with an array of eight emitters (FIG. 2, 220) with multiple emitters (FIG. 2, 220) being active simultaneously or sequentially. As described above, emission characteristics of one of the emitters (FIG. 2, 220) may be altered to, for example, shift constructive and destructive interference in a beam-forming/beam-steering process. For example, a second signal from a second emitter (FIG. 2, 220) may be varied by applying a phase-shifted signal, a noise pattern or to produce a random frequency within a predetermined range. In some examples, the predetermined range may be between 1 MHz and 430 THz or more particularly within 10 MHz to 3 GHz, and even more particularly between 10 MHz and 1 GHz.

In some examples, a patient's response to the TEMT may be determined and treatment parameters may be altered during a subsequent TEMT based on such a response. For example, as indicated earlier due to any number of reasons, different patients may respond differently to TEMT with different treatment parameters. As a specific example, the initial treatment parameters may be selected based on an estimate of protein β-amyloid (Aβ) in a brain of a patient. Following a determination of user response, which may be based on cognitive monitoring as described above, the treatment parameters may be adjusted. As described above, the response of a patient to the TEMT may be based on user characteristics such as hair thickness, skull thickness, etc. The parameters that may be adjusted are wide and include for example frequency, pulse rate, duration, modality, and power level.

Figure 10:
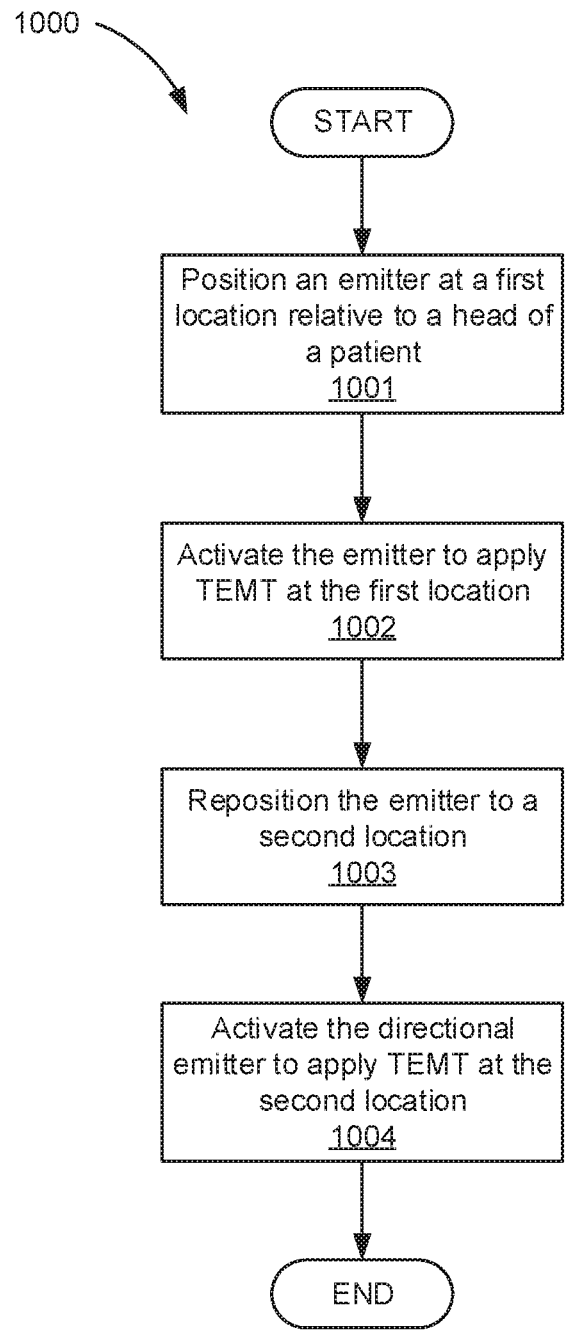
FIG. 10 is a method for transcranial electromagnetic treatment (TEMT), according to another example of the principles described herein.

FIG. 10 is a flowchart for a method (1000) for TEMT, according to another example of the principles described herein. According to the method, an emitter (FIG. 2, 220) of a TEMT system (FIG. 2, 200) is positioned (block 1001) at a first location relative to a head of a patient. As with other emitters (220) described above, the emitter (220) may be placed proximate to the head of the patient or in contact with the head of the patient. The emitter (FIG. 2, 220) is activated (block 1002) to apply transcranial electromagnetic treatment (TEMT) with the emitter (FIG. 2, 220) at the first location to disaggregate Aβ or tau oligomers.

The method (1000) includes repositioning (block 1003) the emitter (FIG. 2, 220) to a second location relative to the head of the patient. In one example, the second location is located on an opposite side of the head from the first location and may be selected to provide coverage of a target structure in the brain.

Following repositioning (block 1003), the emitter (FIG. 2, 220) is again activated (block 1004) to apply TEMT with the emitter at the second location. The TEMT at the second location may have the same or different parameters as the TEMT applied at the first location. That is, the waveform, frequency, etc. for both the first TEMT session and the second TEMT session may be different or the same when applied at either location.

In some examples, the TEMT parameters are selected based on the first and second locations so as to maximize treatment of a target tissue. For example, a treatment applied near the temple may have a different wavelength, pulse frequency, duration, or other parameter than a treatment applied to an anterior portion of the head. This may be especially true when dealing with hair and similar features which may impact the standoff between the emitter and the target tissue.

The emitter (FIG. 2, 220) may be sequentially repositioned to different locations and activated to disaggregate Aβ or tau oligomers at different locations of the head of the patient. Such a method (100) may be carried out using a portable/handheld device as depicted in FIG. 6.

Figure 11A:
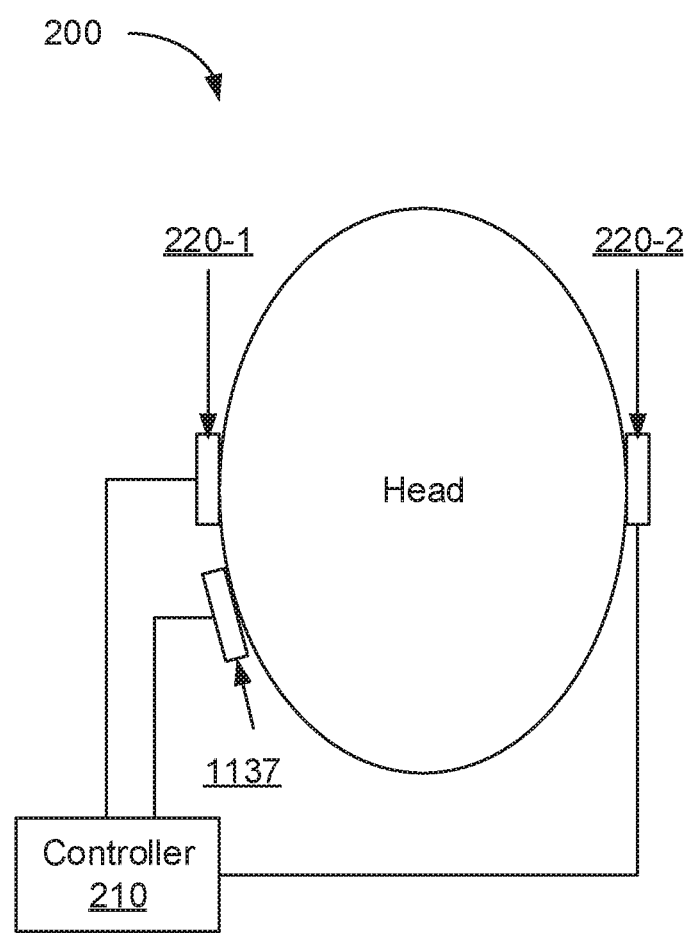
FIGS. 11A and 11B are overhead views of different TEMT systems, according to examples of the principles described herein.
Figure 11B:
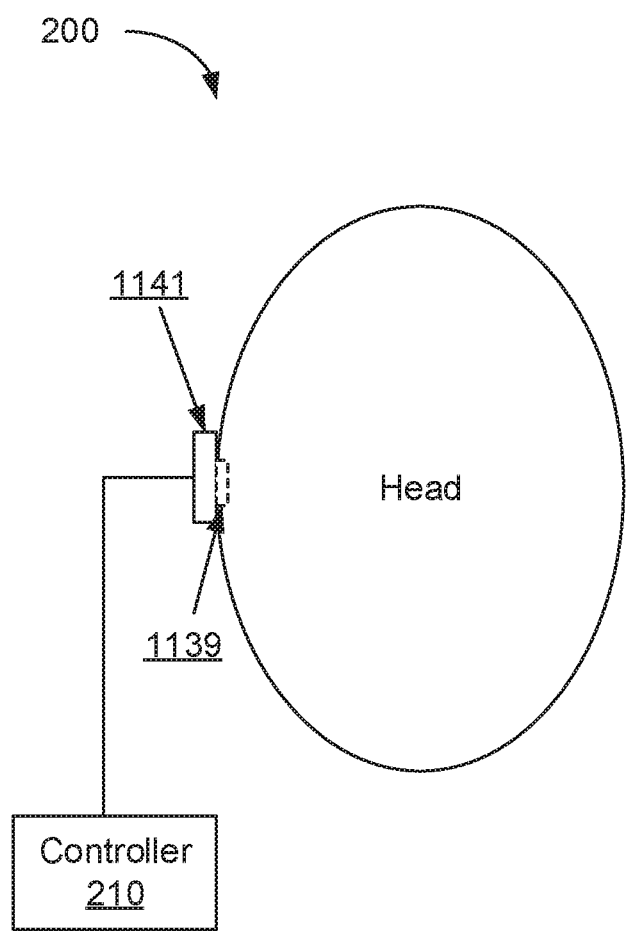

FIGS. 11A and 11B are overhead views of different TEMT systems (200), according to examples of the principles described herein. Specifically, FIG. 11A depicts a TEMT system (200) with a first emitter (220-1) in electrical contact with a scalp of a patient. As described above, in these examples the controller (210) may control the emitters (220-1, 220-2) to emit signals with a frequency between 1 MHz and 430 THz and more particularly between 1 MHz and 3 GHz. In this example, at least a second emitter (220-2) and in some cases an array of additional emitters (220) may also be in electrical contact with the scalp of the patient. In some particular examples, this contact may be through a conductive adhesive. In some examples, in addition to the emitters (220-1, 220-2), the TEMT system (200) may include a return emitter (1137) in contact with the skin of the patient and paired with each respective emitter. For simplicity just one return emitter (1137) is depicted, which return emitter (1137) is paired with the second emitter (220-2).

FIG. 11B depicts a TEMT system (200) that includes a subcutaneous implant (1139) which includes a controller (FIG. 2, 210) and emitter (FIG. 2, 220). In this example, the TEMT system (200) also includes a power source (1141). In some examples, the power source is disposed within the subcutaneous implant (1139). In other examples, the power source (1141) is external to the head and is inductively coupled to the subcutaneous implant (1139) through a head of a user to provide power to the subcutaneous implant (1139). To adhere the power source (1141), the TEMT system (200) may include a first magnet in the subcutaneous implant (1139) and a second magnet associated with the power source (1141). These magnets align the power source (1141) and the subcutaneous implant (1139).

As the subcutaneous implant (1139) is internal to the patient, a mechanism for charging the controller (FIG. 2, 210) is provided in the current TEMT system (200). Accordingly, in one example, the subcutaneous implant (1139) includes a capacitor to receive energy inductively from the power source (1141) and to provide energy to the emitter (FIG. 2, 220) of the subcutaneous implant.

Figure 12:
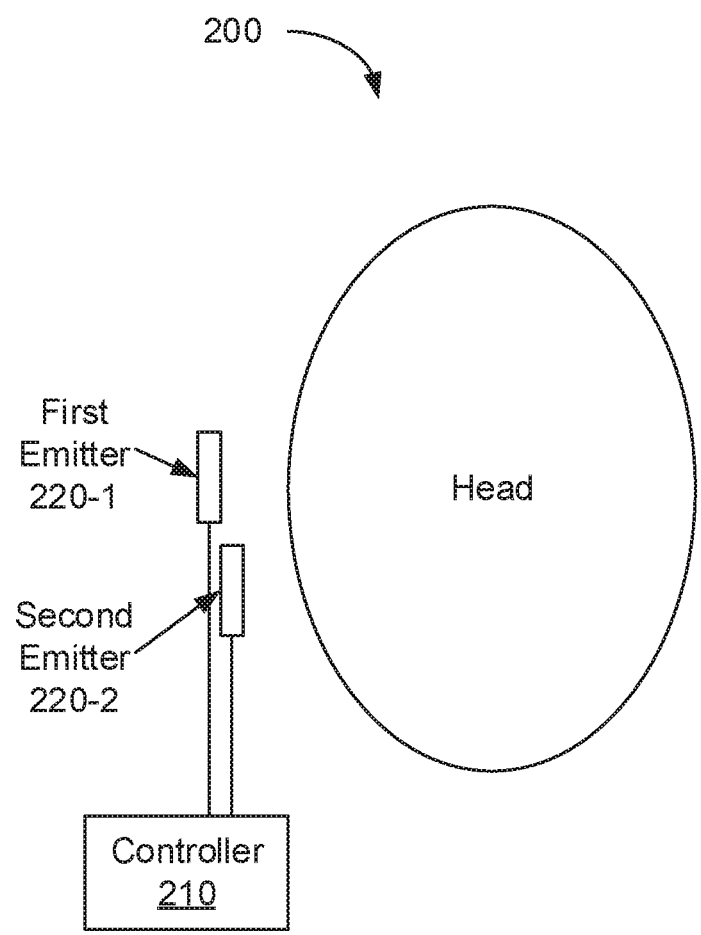
FIG. 12 depicts a system for treatment for protein oligomers in neural tissue, according to an example of the principles described herein.

FIG. 12 depicts a system (200) for prevention or treatment of toxic protein oligomers (such as Aβ and tau oligomers) in neural tissue, according to an example of the principles described herein. As described above, the system (200) includes an array of emitters (220) including at least a first emitter (220-1) and a second emitter (220-2). In this example, the first emitter (220-1) and the second emitter (220-2) are positioned to direct signals toward a brain of a patient. FIG. 12 also depicts the controller (210) that simultaneously directs the first emitter (220-1) to broadcast a first signal toward the brain of the patient and direct the second emitter (220-2) to broadcast a second signal toward the brain of the patient. In some examples, the controller (210) may provide a frequency offset and or a phase offset between the first signal and second signal to steer an emission beam.

In addition to the emitters (220) depicted in FIG. 12, the system (200) may include additional emitters (220) also positioned to direct signals toward the brain and that are also controlled simultaneously by the controller (210) to broadcast signals toward the brain of the patient, which signals may be the same or different from one another.

Figure 13:
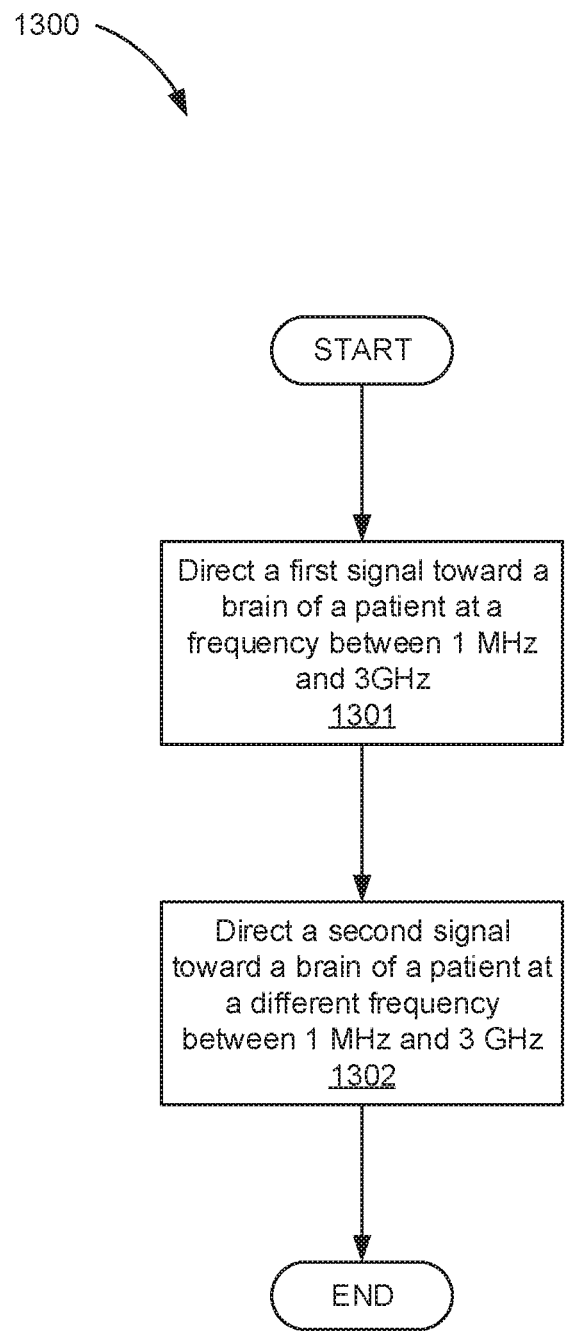
FIG. 13 is a flowchart of a method of administering transcranial electromagnetic treatment (TEMT), according to an example of the principles described herein.

FIG. 13 is a flowchart of a method (1300) of administering transcranial electromagnetic treatment (TEMT), according to an example of the principles described herein. According to the method (1300), a first signal is directed (block 1301) toward a brain of a patient from a first emitter (FIG. 2, 220), which first signal is at a frequency of between 1 MHz and 3 GHz. A second signal is also directed (block 1302) towards the brain of the patient from the first emitter (FIG. 2, 220) wherein the second signal is also at a frequency between 1 MHz and 3 GHz, but at a different frequency than the first. As a particular example, the frequencies of the first and second signals differ by at least 10% of the larger frequency. In yet another specific example, the frequencies of the first and second signals differ by 1 to 10% of the larger frequency.

The preceding description has been presented only to illustrate and describe the invention. It is not intended to be exhaustive or to limit the invention to any precise form disclosed. Many modifications and variations are possible in light of the above teaching.

The examples descried herein were chosen and described in order to best explain the principles of the subject matter and its practical application. The preceding description is intended to enable others skilled in the art to best utilize the subject matter in various embodiments and with various modifications as are suited to the particular use contemplated.

What is claimed is:

1. A method for treating formation of amyloid oligomers, comprising:
   positioning a first emitter and a second emitter of a transcranial electromagnetic treatment (TEMT) system having multiple emitters at a location relative to a head of a patient such that the first emitter and the second emitter emit electromagnetic frequency signals toward the head of the patient; and
   disaggregating amyloid oligomers in neurons of the patient by activating the first emitter and the second emitter to apply TEMT to the patient, the first emitter and the second emitter to operate at different frequencies.

2. The method of claim 1, wherein the emitters emit a continuous signal with a frequency between 1 megahertz (MHz) and 450 terahertz (THz).

3. The method of claim 1, wherein a first signal frequency and a second signal frequency are between 1 MHz and 3 gigahertz (GHz).

4. The method of claim 1, further comprising:
   determining a response of the patient to the TEMT; and
   altering treatment parameters during a subsequent TEMT based on the response of the patient to the TEMT.

5. The method of claim 4, wherein:
   the treatment parameters are selected from the group consisting of frequency, pulse rate, duration, and power level; and
   the treatment parameters are selected based on an estimate of Alzheimer's markers such as A-beta (Aβ) or tau oligomers in the blood, cerebrospinal fluid, or brain of the patient.

6. The method of claim 1, wherein the TEMT has:
   a primary frequency of 1 MHz to 3 GHz;
   a pulse repetition rate of 10 Hz to 300 Hz; and
   a duty cycle between 1% and 100%.

7. The method of claim 1, wherein:
   the method comprises:

directing the first emitter to broadcast a first signal toward the brain of the patient to disaggregate amyloid oligomers; and directing the second emitter to broadcast a second signal toward the brain of the patient to disaggregate amyloid oligomers; and the first signal and the second signal are directed to a same area of the brain.

8. The method of claim 7, wherein the first signal and the second signal differ with regards to at least one of power level, modality, continuous or pulsed, phase, and pulse repetition rate.

9. A transcranial electromagnetic treatment (TEMT) system having multiple emitters for treating formation of amyloid oligomers, comprising:

an emitter array comprising a plurality of emitters to emit electromagnetic frequency signals; and a controller to control emission of electromagnetic radiation from each of the emitters by:

directing a first emitter to broadcast a first signal with a first frequency toward a brain of a patient to disaggregate amyloid oligomers in neurons of the brain of the patient by disrupting hydrogen bonding within the amyloid oligomers in the neurons; and directing a second emitter to broadcast a second signal with a second frequency that is different than the first frequency toward the brain of the patient to disaggregate amyloid oligomers in neurons of the brain of the patient by disrupting hydrogen bonding within the amyloid oligomers in the neurons.

10. The TEMT system of claim 9, wherein the TEMT system is a handheld device that comprises the controller and emitter array.

11. The TEMT system of claim 9, wherein the TEMT system comprises:

a handheld device that comprises the emitter array; and a second device that comprises the controller and that is coupled via cable to the handheld device.

12. The TEMT system of claim 9:

further comprising a head device to be placed over the patient; and wherein the emitter array is disposed in the head device.

13. The TEMT system of claim 12, wherein the head device is lowered relative to a patient underneath the head device.

14. The TEMT system of claim 12:

further comprising a distance sensor to detect a position of the head device relative to the head of the patient; and wherein the controller receives an output of the distance sensor to modify treatment parameters.

15. The TEMT system of claim 9, wherein emitters of the array are activated in sequence.

16. The TEMT system of claim 9, wherein multiple emitters of the array are active simultaneously.

17. The TEMT system of claim 9, wherein the controller varies a phase between the first signal and the second signal to steer an emission beam.

18. The TEMT system of claim 9, further comprising a treatment status indicator to indicate a status of the treatment.

19. The TEMT system of claim 9, wherein the first emitter and the second emitter are in electrical contact with a scalp of the patient.

20. The TEMT system of claim 19, further comprising an array of return emitters in contact with skin of the patient, wherein each return emitter is paired with an emitter of the array.

21. A method for treating formation of amyloid oligomers, comprising:

positioning an emitter of a transcranial electromagnetic treatment (TEMT) system at a first location relative to a head of a patient;

activating the emitter to apply transcranial electromagnetic treatment (TEMT) at a first frequency with the emitter at the first location to disaggregate at least one of A-beta (Aβ), tau, p-tau, and alpha-synuclein oligomers in neurons of the patient;

repositioning the emitter to a second location relative to the head of the patient; and activating the emitter to apply TEMT at a second frequency that differs from the first frequency with the directional emitter at the second location to disaggregate at least one of Aβ, tau, p-tau, and alpha-synuclein oligomers in the neurons of the patient.

22. The method of claim 21, wherein the emitter is active between 5 minutes to 120 minutes delivering between 0.1 W/kg to 8.0 W/kg average specific absorption rate (SAR).

23. The method of claim 21, further comprising repeating application of TEMT daily for at least 2 days.

24. A transcranial electromagnetic treatment (TEMT) system for treating formation of amyloid oligomers, comprising:

a subcutaneous implant comprising:

multiple emitters to emit electromagnetic frequency signals with frequencies between 1 megahertz (MHz) and 430 terahertz (THz) wherein a first emitter to emit a first signal with a first frequency and a second emitter to emit a second signal with a second frequency that differs from the first signal, the first and second signals directed toward a brain of a patient to disaggregate amyloid oligomers in neurons of the brain; and a controller to control emission of radiation from the emitter; and a power source to provide power to the subcutaneous implant.

25. The TEMT system of claim 24, wherein the power source is disposed within the subcutaneous implant.

26. The TEMT system of claim 24, wherein the power source is external and is inductively coupled to the subcutaneous implant through a head of the user.

27. The TEMT system of claim 24, further comprising at least one of:

a first magnet in the subcutaneous implant and a second magnet associated with an external power source, the first and second magnets to align the external power source with the subcutaneous implant; and a power receiver in the subcutaneous implant to receive energy inductively from the external power source and provide energy to the emitter of the subcutaneous implant.

* * * * *